US008317856B2

(12) United States Patent
Shalev et al.

(10) Patent No.: US 8,317,856 B2
(45) Date of Patent: Nov. 27, 2012

(54) MULTI-COMPONENT EXPANDABLE SUPPORTIVE BIFURCATED ENDOLUMINAL GRAFTS AND METHODS FOR USING SAME

(75) Inventors: Alon Shalev, Raanana (IL); Rafi Benary, Tel Aviv (IL)

(73) Assignee: Endospan Ltd., Netanya (IL)

( * ) Notice: Subject to any disclaimer, the term of this patent is extended or adjusted under 35 U.S.C. 154(b) by 216 days.

(21) Appl. No.: 12/529,936

(22) PCT Filed: Mar. 5, 2008

(86) PCT No.: PCT/IL2008/000287
§ 371 (c)(1),
(2), (4) Date: Sep. 4, 2009

(87) PCT Pub. No.: WO2008/107885
PCT Pub. Date: Sep. 12, 2008

(65) Prior Publication Data
US 2010/0063575 A1    Mar. 11, 2010

Related U.S. Application Data

(60) Provisional application No. 60/892,885, filed on Mar. 5, 2007, provisional application No. 60/991,726, filed on Dec. 2, 2007.

(51) Int. Cl.
*A61F 2/82* (2006.01)
(52) U.S. Cl. ............... 623/1.35; 623/1.15; 623/1.13
(58) Field of Classification Search ............ 623/1.13, 623/1.15, 1.35
See application file for complete search history.

(56) References Cited

U.S. PATENT DOCUMENTS

| | | | |
|---|---|---|---|
| 4,355,426 A | 10/1982 | MacGregor |
| 4,505,767 A | 3/1985 | Quin |
| 4,562,596 A | 1/1986 | Kornberg |
| 4,577,631 A | 3/1986 | Kreamer |
| 4,617,932 A | 10/1986 | Kornberg |
| 4,665,906 A | 5/1987 | Jervis |
| 4,739,762 A | 4/1988 | Palmaz |
| 4,787,899 A | 11/1988 | Lazarus |
| 4,878,906 A | 11/1989 | Lindemann et al. |
| 4,886,062 A | 12/1989 | Wiktor |
| 4,938,740 A | 7/1990 | Melbin |
| 4,969,458 A | 11/1990 | Wiktor |
| 5,042,707 A | 8/1991 | Taheri |

(Continued)

FOREIGN PATENT DOCUMENTS

CA    2 497 704    3/2004

(Continued)

OTHER PUBLICATIONS

International Search Report dated Sep. 29, 2008 in corresponding International Application No. PCT/IL2008/000287.

(Continued)

*Primary Examiner* — Christopher D Koharski
*Assistant Examiner* — Jason-Dennis Stewart
(74) *Attorney, Agent, or Firm* — Sughrue Mion, PLLC

(57) ABSTRACT

A multiple-component expandable endoluminal system for treating a lesion at a bifurcation including a self expandable tubular root member having a side-looking engagement aperture, a self expandable tubular trunk member comprising a substantially blood impervious polymeric liner secured therealong; both having a radially compressed state adapted for percutaneous intraluminal delivery and a radially expanded state adapted for endoluminal support.

24 Claims, 9 Drawing Sheets

U.S. PATENT DOCUMENTS

| | | | |
|---|---|---|---|
| 5,064,435 A | 11/1991 | Porter | |
| 5,122,136 A | 6/1992 | Guglielmi et al. | |
| 5,133,732 A | 7/1992 | Wiktor | |
| 5,486,183 A | 1/1996 | Middleman et al. | |
| 5,507,769 A | 4/1996 | Marin et al. | |
| 5,509,923 A | 4/1996 | Middleman et al. | |
| 5,522,880 A | 6/1996 | Barone et al. | |
| 5,527,322 A | 6/1996 | Klein et al. | |
| 5,554,181 A | 9/1996 | Das | |
| 5,562,724 A | 10/1996 | Vorwerk et al. | |
| 5,613,974 A | 3/1997 | Andreas et al. | |
| 5,632,746 A | 5/1997 | Middleman et al. | |
| 5,632,763 A | 5/1997 | Glastra | |
| 5,632,772 A * | 5/1997 | Alcime et al. | 623/1.35 |
| 5,639,278 A | 6/1997 | Dereume et al. | |
| 5,643,340 A | 7/1997 | Nunokawa | |
| 5,653,743 A * | 8/1997 | Martin | 623/1.35 |
| 5,676,696 A * | 10/1997 | Marcade | 623/1.35 |
| 5,676,697 A * | 10/1997 | McDonald | 623/1.35 |
| 5,728,134 A | 3/1998 | Barak | |
| 5,749,879 A | 5/1998 | Middleman et al. | |
| 5,755,770 A | 5/1998 | Ravenscroft | |
| 5,755,771 A | 5/1998 | Penn et al. | |
| 5,755,777 A | 5/1998 | Chuter | |
| 5,769,882 A | 6/1998 | Fogarty et al. | |
| 5,782,903 A | 7/1998 | Wiktor | |
| 5,782,906 A | 7/1998 | Marshall et al. | |
| 5,824,040 A | 10/1998 | Cox et al. | |
| 5,860,991 A | 1/1999 | Klein et al. | |
| 5,876,432 A | 3/1999 | Lau et al. | |
| 5,906,641 A | 5/1999 | Thompson et al. | |
| 5,921,994 A | 7/1999 | Andreas et al. | |
| 5,948,018 A * | 9/1999 | Dereume et al. | 623/1.12 |
| 6,015,431 A | 1/2000 | Thornton et al. | |
| 6,033,435 A | 3/2000 | Penn et al. | |
| 6,059,824 A | 5/2000 | Taheri | |
| 6,099,497 A | 8/2000 | Adams et al. | |
| 6,117,145 A | 9/2000 | Wood et al. | |
| 6,200,339 B1 | 3/2001 | Leschinsky et al. | |
| 6,206,893 B1 | 3/2001 | Klein et al. | |
| 6,270,524 B1 | 8/2001 | Kim | |
| 6,283,991 B1 | 9/2001 | Cox et al. | |
| 6,290,720 B1 | 9/2001 | Khosravi et al. | |
| 6,325,823 B1 | 12/2001 | Horzewski et al. | |
| 6,428,565 B1 * | 8/2002 | Wisselink | 623/1.11 |
| 6,506,211 B1 | 1/2003 | Skubitz et al. | |
| 6,613,078 B1 | 9/2003 | Barone | |
| 6,635,083 B1 | 10/2003 | Cheng et al. | |
| 6,652,567 B1 | 11/2003 | Deaton | |
| 6,656,214 B1 | 12/2003 | Fogarty et al. | |
| 6,692,520 B1 | 2/2004 | Gambale et al. | |
| 6,695,833 B1 | 2/2004 | Frantzen | |
| 6,733,523 B2 * | 5/2004 | Shaolian et al. | 623/1.35 |
| 6,743,195 B2 | 6/2004 | Zucker | |
| 6,776,794 B1 | 8/2004 | Hong et al. | |
| 6,814,749 B2 | 11/2004 | Cox et al. | |
| 6,814,752 B1 | 11/2004 | Chuter | |
| 6,824,560 B2 | 11/2004 | Pelton | |
| 6,846,321 B2 | 1/2005 | Zucker | |
| 6,907,285 B2 | 6/2005 | Denker et al. | |
| 6,908,477 B2 * | 6/2005 | McGuckin et al. | 623/1.11 |
| 6,929,660 B1 | 8/2005 | Ainsworth et al. | |
| 6,942,691 B1 * | 9/2005 | Chuter | 623/1.35 |
| 6,964,679 B1 | 11/2005 | Marcade et al. | |
| 6,986,774 B2 | 1/2006 | Middleman et al. | |
| 7,008,441 B2 | 3/2006 | Zucker | |
| 7,044,962 B2 | 5/2006 | Elliott | |
| 7,105,020 B2 | 9/2006 | Greenberg et al. | |
| 7,112,217 B1 | 9/2006 | Kugler et al. | |
| 7,115,127 B2 | 10/2006 | Lindenbaum et al. | |
| 7,144,421 B2 | 12/2006 | Carpenter et al. | |
| 7,160,318 B2 * | 1/2007 | Greenberg et al. | 623/1.13 |
| 7,201,772 B2 | 4/2007 | Schwammenthal et al. | |
| 7,223,266 B2 | 5/2007 | Lindenbaum et al. | |
| 7,279,003 B2 | 10/2007 | Berra et al. | |
| 7,306,623 B2 * | 12/2007 | Watson | 623/1.16 |
| 7,341,598 B2 | 3/2008 | Davidson et al. | |
| 7,407,509 B2 | 8/2008 | Greenberg et al. | |
| 7,425,219 B2 * | 9/2008 | Quadri | 623/1.35 |
| 7,429,269 B2 | 9/2008 | Schwammenthal et al. | |
| 7,442,204 B2 | 10/2008 | Schwammenthal et al. | |
| 7,473,272 B2 | 1/2009 | Pryor | |
| 7,537,609 B2 | 5/2009 | Davidson et al. | |
| 7,540,881 B2 | 6/2009 | Meyer et al. | |
| 7,544,160 B2 | 6/2009 | Gross | |
| 7,637,939 B2 | 12/2009 | Tischler | |
| 7,662,161 B2 | 2/2010 | Briganti et al. | |
| 7,662,168 B2 | 2/2010 | McGuckin, Jr. et al. | |
| 7,678,141 B2 | 3/2010 | Greenan et al. | |
| 7,722,626 B2 | 5/2010 | Middleman et al. | |
| 7,731,732 B2 | 6/2010 | Ken | |
| 7,815,673 B2 | 10/2010 | Bloom et al. | |
| 7,959,662 B2 | 6/2011 | Erbel et al. | |
| 2001/0014823 A1 | 8/2001 | Ressemann et al. | |
| 2001/0037142 A1 * | 11/2001 | Stelter et al. | 623/1.13 |
| 2001/0044652 A1 | 11/2001 | Moore | |
| 2001/0053930 A1 | 12/2001 | Kugler et al. | |
| 2002/0052643 A1 * | 5/2002 | Wholey et al. | 623/1.13 |
| 2002/0072790 A1 * | 6/2002 | McGuckin et al. | 623/1.12 |
| 2002/0099441 A1 | 7/2002 | Dehdashtian | |
| 2002/0123791 A1 | 9/2002 | Harrison | |
| 2002/0156495 A1 | 10/2002 | Brenneman et al. | |
| 2003/0033005 A1 * | 2/2003 | Houser et al. | 623/1.35 |
| 2003/0093145 A1 | 5/2003 | Lawrence-Brown et al. | |
| 2003/0130720 A1 | 7/2003 | DePalma et al. | |
| 2003/0153968 A1 | 8/2003 | Geis et al. | |
| 2003/0199967 A1 | 10/2003 | Hartley et al. | |
| 2003/0212449 A1 | 11/2003 | Cox | |
| 2003/0236567 A1 | 12/2003 | Elliot | |
| 2004/0015227 A1 | 1/2004 | Vardi et al. | |
| 2004/0106972 A1 | 6/2004 | Deaton | |
| 2004/0106978 A1 | 6/2004 | Greenberg et al. | |
| 2004/0117003 A1 * | 6/2004 | Ouriel et al. | 623/1.35 |
| 2004/0133266 A1 | 7/2004 | Clerc et al. | |
| 2004/0138735 A1 * | 7/2004 | Shaolian et al. | 623/1.11 |
| 2004/0171978 A1 | 9/2004 | Shalaby | |
| 2004/0181149 A1 | 9/2004 | Langlotz et al. | |
| 2004/0215327 A1 | 10/2004 | Doig et al. | |
| 2004/0260383 A1 * | 12/2004 | Stelter et al. | 623/1.11 |
| 2005/0033406 A1 | 2/2005 | Barnhart et al. | |
| 2005/0049678 A1 | 3/2005 | Cocks et al. | |
| 2005/0065545 A1 | 3/2005 | Wallace | |
| 2005/0102018 A1 * | 5/2005 | Carpenter et al. | 623/1.11 |
| 2005/0102021 A1 * | 5/2005 | Osborne | 623/1.13 |
| 2005/0131517 A1 | 6/2005 | Hartley et al. | |
| 2005/0149166 A1 | 7/2005 | Schaeffer et al. | |
| 2005/0159803 A1 * | 7/2005 | Lad et al. | 623/1.13 |
| 2005/0165480 A1 * | 7/2005 | Jordan et al. | 623/9 |
| 2005/0171598 A1 | 8/2005 | Schaeffer | |
| 2005/0171599 A1 * | 8/2005 | White | 623/1.36 |
| 2005/0203606 A1 | 9/2005 | VanCamp | |
| 2005/0222668 A1 | 10/2005 | Schaeffer et al. | |
| 2005/0222669 A1 | 10/2005 | Purdy | |
| 2005/0273155 A1 * | 12/2005 | Bahler et al. | 623/1.13 |
| 2006/0015170 A1 | 1/2006 | Jones et al. | |
| 2006/0030921 A1 * | 2/2006 | Chu | 623/1.11 |
| 2006/0052799 A1 | 3/2006 | Middleman et al. | |
| 2006/0069426 A1 | 3/2006 | Weinberger | |
| 2006/0100684 A1 | 5/2006 | Elliott | |
| 2006/0116748 A1 * | 6/2006 | Kaplan et al. | 623/1.11 |
| 2006/0149360 A1 | 7/2006 | Schwammenthal et al. | |
| 2006/0155358 A1 | 7/2006 | LaDuca et al. | |
| 2006/0155359 A1 * | 7/2006 | Watson | 623/1.13 |
| 2006/0155366 A1 | 7/2006 | LaDuca et al. | |
| 2006/0167476 A1 | 7/2006 | Burdulis, Jr. et al. | |
| 2006/0193892 A1 | 8/2006 | Furst et al. | |
| 2006/0229709 A1 | 10/2006 | Morris et al. | |
| 2006/0241740 A1 * | 10/2006 | Vardi et al. | 623/1.16 |
| 2006/0281966 A1 | 12/2006 | Peacock, III | |
| 2007/0021822 A1 | 1/2007 | Boatman | |
| 2007/0043425 A1 | 2/2007 | Hartley et al. | |
| 2007/0055350 A1 | 3/2007 | Erickson et al. | |
| 2007/0055358 A1 | 3/2007 | Krolik et al. | |
| 2007/0055360 A1 * | 3/2007 | Hanson et al. | 623/1.35 |
| 2007/0060989 A1 | 3/2007 | Deem et al. | |
| 2007/0073373 A1 | 3/2007 | Bonsignore | |
| 2007/0088425 A1 | 4/2007 | Schaeffer | |

| Publication No. | Date | Name |
|---|---|---|
| 2007/0112344 A1 | 5/2007 | Keilman |
| 2007/0135677 A1 | 6/2007 | Miller et al. |
| 2007/0142896 A1 | 6/2007 | Anderson et al. |
| 2007/0150051 A1 | 6/2007 | Arnault De La Menardiere et al. |
| 2007/0156167 A1 | 7/2007 | Connors et al. |
| 2007/0167898 A1 | 7/2007 | Peters et al. |
| 2007/0185565 A1 | 8/2007 | Schwammenthal et al. |
| 2007/0208410 A1 | 9/2007 | Berra et al. |
| 2007/0213805 A1 | 9/2007 | Schaeffer et al. |
| 2007/0219610 A1 | 9/2007 | Israel |
| 2007/0225797 A1* | 9/2007 | Krivoruhko .......... 623/1.35 |
| 2007/0233229 A1 | 10/2007 | Berra et al. |
| 2007/0237973 A1 | 10/2007 | Purdy et al. |
| 2007/0244542 A1 | 10/2007 | Greenan et al. |
| 2007/0244543 A1 | 10/2007 | Mitchell |
| 2007/0244547 A1 | 10/2007 | Greenan |
| 2007/0255388 A1 | 11/2007 | Rudakov et al. |
| 2008/0002871 A1* | 1/2008 | Gunzert-Marx et al. ..... 382/132 |
| 2008/0015673 A1 | 1/2008 | Chuter |
| 2008/0058918 A1 | 3/2008 | Watson |
| 2008/0109066 A1 | 5/2008 | Quinn |
| 2008/0114445 A1 | 5/2008 | Melsheimer et al. |
| 2008/0147173 A1 | 6/2008 | McIff et al. |
| 2008/0167704 A1 | 7/2008 | Wright et al. |
| 2008/0269789 A1 | 10/2008 | Eli |
| 2008/0275540 A1 | 11/2008 | Wen |
| 2008/0275542 A1 | 11/2008 | LaDuca et al. |
| 2008/0288044 A1 | 11/2008 | Osborne |
| 2008/0319528 A1 | 12/2008 | Yribarren et al. |
| 2009/0012597 A1 | 1/2009 | Doig et al. |
| 2009/0012602 A1 | 1/2009 | Quadri |
| 2009/0030502 A1* | 1/2009 | Sun et al. ............ 623/1.16 |
| 2009/0048663 A1* | 2/2009 | Greenberg .......... 623/1.35 |
| 2009/0099648 A1 | 4/2009 | Yu |
| 2009/0099649 A1 | 4/2009 | Chobotov et al. |
| 2009/0105809 A1 | 4/2009 | Lee et al. |
| 2009/0112233 A1 | 4/2009 | Xiao |
| 2009/0125096 A1 | 5/2009 | Chu et al. |
| 2009/0138067 A1* | 5/2009 | Pinchuk et al. ......... 623/1.13 |
| 2009/0149877 A1 | 6/2009 | Hanson et al. |
| 2009/0240316 A1 | 9/2009 | Bruszewski |
| 2009/0248134 A1 | 10/2009 | Dierking et al. |
| 2009/0254170 A1 | 10/2009 | Hartley et al. |
| 2009/0259290 A1 | 10/2009 | Bruszewski et al. |
| 2009/0287145 A1 | 11/2009 | Cragg et al. |
| 2010/0063575 A1 | 3/2010 | Shalev |
| 2010/0070019 A1 | 3/2010 | Shalev |
| 2010/0161026 A1 | 6/2010 | Brocker et al. |
| 2010/0292774 A1 | 11/2010 | Shalev |
| 2011/0093002 A1 | 4/2011 | Rucker et al. |
| 2011/0208289 A1 | 8/2011 | Shalev |
| 2011/0208296 A1 | 8/2011 | Duffy et al. |
| 2011/0208297 A1 | 8/2011 | Tuval et al. |
| 2011/0208298 A1 | 8/2011 | Tuval et al. |
| 2011/0218607 A1 | 9/2011 | Arbefeuille et al. |
| 2011/0264184 A1 | 10/2011 | Heltai |

FOREIGN PATENT DOCUMENTS

| | | |
|---|---|---|
| CA | 2497704 A1 | 3/2004 |
| EP | 1 177 780 | 2/2002 |
| EP | 1177780 A2 | 2/2002 |
| EP | 1 325 716 | 7/2003 |
| EP | 1325716 A1 | 7/2003 |
| JP | 2002-253682 | 9/2002 |
| WO | 2004/017868 | 3/2004 |
| WO | 2004017868 A1 | 3/2004 |
| WO | 2005/002466 | 1/2005 |
| WO | 2005002466 A2 | 1/2005 |
| WO | 2005/037138 | 4/2005 |
| WO | 2005/041781 | 5/2005 |
| WO | 2005/041783 | 5/2005 |
| WO | 2006/007389 | 1/2006 |
| WO | 2006007389 A1 | 1/2006 |
| WO | 2006/028925 | 3/2006 |
| WO | 2006/070372 | 7/2006 |
| WO | 2006070372 A2 | 7/2006 |
| WO | 2007/084547 | 7/2007 |
| WO | 2007084547 A1 | 7/2007 |
| WO | 2007/144782 | 12/2007 |
| WO | 2008/140796 | 1/2008 |
| WO | 2008008291 A2 | 1/2008 |
| WO | 2008/035337 | 3/2008 |
| WO | 2008035337 A2 | 3/2008 |
| WO | 2008/042266 | 4/2008 |
| WO | 2008/047092 | 4/2008 |
| WO | 2008/047354 | 4/2008 |
| WO | 2008042266 A2 | 4/2008 |
| WO | 2008047092 A1 | 4/2008 |
| WO | 2008047354 A2 | 4/2008 |
| WO | 2008/053469 | 5/2008 |
| WO | 2008/107885 | 9/2008 |
| WO | 2008140796 A1 | 11/2008 |
| WO | 2009/078010 | 6/2009 |
| WO | 2009/116041 | 9/2009 |
| WO | 2009/116042 | 9/2009 |
| WO | 2009116041 A2 | 9/2009 |
| WO | 2009116042 A2 | 9/2009 |
| WO | 2009/118733 A2 | 10/2009 |
| WO | 2010/024869 | 3/2010 |
| WO | 2010/024879 | 3/2010 |
| WO | 2010/031060 | 3/2010 |
| WO | 2010024869 A1 | 3/2010 |
| WO | 2010024879 A1 | 3/2010 |
| WO | 2010031060 A1 | 3/2010 |
| WO | 2010/045238 | 4/2010 |
| WO | 2010045238 A2 | 4/2010 |
| WO | 2010/062355 | 6/2010 |
| WO | 2010062355 A1 | 6/2010 |
| WO | 2010/088776 | 8/2010 |
| WO | 2010088776 A1 | 8/2010 |
| WO | 2010128162 A1 | 11/2010 |
| WO | 2010/150208 | 12/2010 |
| WO | 2011/004374 | 1/2011 |
| WO | 2011/007354 | 1/2011 |
| WO | 2011/055364 | 5/2011 |
| WO | 2011/064782 | 6/2011 |
| WO | 2011/067764 | 6/2011 |
| WO | 2011/070576 | 6/2011 |
| WO | 2011/080738 | 7/2011 |
| WO | 2011/095979 | 8/2011 |
| WO | 2011/106532 | 9/2011 |
| WO | 2011/106533 | 9/2011 |
| WO | 2011/106544 | 9/2011 |
| WO | 2011106532 A1 | 9/2011 |
| WO | 2011106533 A1 | 9/2011 |
| WO | 2011106544 A1 | 9/2011 |

OTHER PUBLICATIONS

Written Opinion dated Sep. 29, 2008 in corresponding International Application No. PCT/IL2008/000287.

International Preliminary Report on Patentability dated Jan. 12, 2010 in corresponding International Application No. PCT/IL2008/000287.

First Office Action dated Aug. 25, 2011 issued in Chinese Application No. 200880014919.9.

Fonseca et al., Intravascular ultrasound assessment of the novel AngioSculpt scoring balloon catheter for the treatment of complex coronary lesions, J Invasive Cardiol, Jan. 2008, pp. 21-27, vol. 20, No. 1.

English Abstract of Japanese Publication JP 2002-253682, published on Sep. 10, 2002.

An International Search Report dated Feb. 18, 2010, which issued during the prosecution of Applicant's PCT/IL08/000287.

A Written Opinion dated Nov. 12, 2009, which issued during the prosecution of Applicant's PCT/IL08/000287.

An International Search Report dated Apr. 28, 2011, which issued during the prosecution of Applicant's PCT/IB2010/052861.

A Written Opinion dated Dec. 23, 2011, which issued during the prosecution of Applicant's PCT/IB2010/052861.

An International Search Report dated Dec. 3, 2010, which issued during the prosecution of Applicant's PCT/IL2010/000564.

A Written Opinion dated Jan. 14, 2012, which issued during the prosecution of Applicant's PCT/IL2010/000564.

An International Search Report dated Nov. 5, 2010, which issued during the prosecution of Applicant's PCT/IL2010/000549.

A Written Opinion dated Jan. 9, 2012, which issued during the prosecution of Applicant's PCT/IL2010/000549.

An International Search Report dated Oct. 6, 2011, which issued during the prosecution of Applicant's PCT/IL2010/000999.

An International Search Report dated Mar. 10, 2011, which issued during the prosecution of Applicant's PCT/IL2010/000917.

An International Search Report dated Jun. 9, 2011, which issued during the prosecution of Applicant's PCT/IL2010/001018.

An International Search Report dated Jun. 16, 2011, which issued during the prosecution of Applicant's PCT/IL2010/001037.

An International Search Report dated Jul. 7, 2011, which issued during the prosecution of Applicant's PCT/IL2010/001087.

An International Search Report dated Aug. 11, 2011, which issued during the prosecution of Applicant's PCT/IL2011/000135.

An International Search Report dated Mar. 11, 2010, which issued during the prosecution of Applicant's PCT/IL2008/001621.

A Written Opinion dated Jun. 15, 2010, which issued during the prosecution of Applicant's PCT/IL2008/001621.

An International Search Report dated Sep. 3, 2009, which issued during the prosecution of Applicant's PCT/IL2007/001312.

A Written Opinion dated Jul. 31, 2009, which issued during the prosecution of Applicant's PCT/IL2007/001312.

An English translation of an Office Action dated Aug. 25, 2011, which issued during the prosecution of Chinese Patent Application No. 200880014919.9.

An Office Action dated Nov. 12, 2010, which issued during the prosecution of U.S. Appl. No. 12/447,684.

An Office Action dated Apr. 27, 2011, which issued during the prosecution of U.S. Appl. No. 12/447,684.

"E-vita® open plus" product brochure (JOTEC GmbH, Hechingen, Germany), 2010.

Fonseca A et al., "Intravascular ultrasound assessment of the novel AngioSculpt scoring balloon catheter for the treatment of complex coronary lesions," J Invasive Cardiol 20(1):21-7 (Jan. 2008).

Khlif H et al., "Contribution to the Improvement of Textile Vascular Prostheses Crimping," Trends in Applied Sciences Research 6(9):1019-1027 (2011).

* cited by examiner

US 8,317,856 B2

MULTI-COMPONENT EXPANDABLE SUPPORTIVE BIFURCATED ENDOLUMINAL GRAFTS AND METHODS FOR USING SAME

CROSS-REFERENCE TO RELATED APPLICATIONS

The present application is the US National Stage of International Patent Application PCT/IL2008/000287, filed Mar. 5, 2008, which claims the benefit of U.S. Provisional Applications 60/892,885, filed Mar. 5, 2007, and 60/991,726, filed Dec. 2, 2007.

FIELD OF THE INVENTION

The present invention relates generally to endoluminal grafts, and particularly to bifurcated endoluminal grafts.

BACKGROUND OF THE INVENTION

For a few decades, conventional treatment of abdominal aortic aneurysms (AAA) was limited either to a sit-and-wait strategy, or in cases with too high a risk for aneurysm rupture, a surgical operation using vascular grafts introduced in major open abdominal surgery.

While long term clinical results of the surgical approach were favorable and the treated patients did not need frequent follow-ups, nevertheless the short-term morbidity, including complication rate, hospitalization time, out-of-work period and related expenses warranted continued search for a less invasive, but still definitive, solution of the problem.

Numerous attempts have been made to introduce such definitive treatments to AAA that involve less morbidity, a shorter hospitalization period and lower related costs, and enable the patient to return to routine life sooner. These initiatives resulted in various endovascular stent-grafts that are commercially available or are being clinically and pre-clinically evaluated. A major advantage in these newer devices is that their implantation involves a significantly less invasive procedure, including creating an endovascular working channel—usually via an incision in the groin area—to the diseased abdominal aorta, through which a self expandable stent-graft is typically introduced. In most cases, a bifurcated device is employed, either in one piece, or in some cases, smaller caliber iliac-grafts are deployed subsequently after the main aortic devices have been well positioned.

Nonetheless, the relatively new endovascular approach has its share of problems and limitations. Some of the major outstanding problems include:

The implantation is complicated because most AAA stent grafts are implanted via two working channels, one in each side of the groin. The interventional radiologist typically has to introduce one main piece of the device via one working channel and an extension piece through the other side in a non trivial manner.

There is a prolonged implantation procedure caused by a difficulty to correctly position the stent-graft and the inability to correct its position once deployed, usually due to barbs that penetrate the aortic wall and anchor the graft thereto. This also involves relatively high doses of X-ray radiation, to which the patient and the staff are exposed during the prolonged endovascular procedure.

In earlier AAA stent grafts, device migration was a major issue, sometimes leading to obstruction of blood flow into the neighboring renal arteries or in other cases exposing the aneurysm to renewed blood penetration. Conventional AAA stent-grafts were typically prone to migration since they are essentially built along a single longitudinal axis and they may migrate along the same axis.

Endovascular leaks (in short—endoleaks) are another problem. Two types of endoleaks are defined: A type I endoleak is leakage of blood around the stent-graft and into the aneurismal sac, which may lead to rupturing the aneurysm. A Type II endoleak occurs when blood/plasma leaks through the graft wall and into the aneurismal space. Type II endoleaks have been mostly resolved by the introduction of finer-woven graft fabrics, performing pre-clotting procedures and/or incorporation of collagen or other procoagulation materials into the graft wall. Type I endoleaks are nonetheless more difficult to prevent and treat.

The device cost is very high. Current self-expandable AAA stent-grafts are usually bifurcated grafts, one piece or multi-piece devices. The connection with the graft fabric is typically achieved by hand stitching to a metallic, self-expandable frame. Hand labor related issues together with the critical QA/QC standards with which these devices have to comply make these devices quite expensive to manufacture.

There are the necessary follow-ups which are time consuming.

SUMMARY OF THE INVENTION

The present invention seeks to provide novel bifurcated endoluminal grafts that overcome the abovementioned problems of the prior art, as described more in detail hereinbelow. The present invention seeks to reduce the laborious and complicated multi-step medical procedures and related cost of the device. The present invention involves significantly fewer, simpler, quicker and more definitive medical steps. The present invention uses simpler device modules, which make the endovascular treatment of AAA quicker, safer for the patient and the treating staff, more reliable and cheaper.

The present invention can reduce the number of vascular access sites from two femoral arteries in both sides of the groin to a single vascular access site. The present invention can reduce the risk of device migration in AAA stent grafts.

There is provided in accordance with an embodiment of the invention a stent graft system including a first component 60 including a tubular structure having a support element 63 and a covering element 62 attached thereto, the first component 60 being positionable in first and second branches that bridge a main trunk of a subject and wherein the first and second elements have an opening 61 arranged to face the main trunk, and a second component 70 having a generally cylindrical form with a support element 72 and a covering element 71 attached thereto, the second component 70 configured to be at least partially disposed within the first component 60 outwardly extending from the opening 61 in the first component 60.

One or both of the first and second components may be adapted for transluminal delivery for transport to a site within a body lumen by being radially compressed from a larger cross-section to a smaller cross-section.

In accordance with an embodiment of the invention the covering element of the first component only partially covers the support element of the first component.

In accordance with an embodiment of the invention the covering element of the second component only partially covers the support element of the second component.

Further in accordance with an embodiment of the invention the first and second components are radially compressible from a larger cross-section to a smaller cross-section, and wherein the first and second components are adapted for transluminal delivery for transport to a site within a body lumen, and wherein the second component is adapted for transluminal delivery through the first component in its larger cross-section and to outwardly extend from the opening in the first component. For example, the first component in its larger cross-section may be dimensioned to intraluminally fit iliac arteries of a subject and the second component in its larger cross-section may be dimensioned to intraluminally fit an abdominal aorta of the subject.

In accordance with an embodiment of the invention the second component includes a proximal segment and a distal segment, and wherein the covering element substantially spans the distal segment but does not generally span the proximal segment. The proximal segment may be dimensioned to be anchorably disposed within the first component. The proximal segment of the second component may be substantially disposed within the first component. The distal segment of the second component may outwardly extend from the opening in the first component.

There is provided in accordance with an embodiment of the invention a method including implanting a stent graft system into a bifurcation in a body lumen, the bifurcation including a main trunk and first and second branches, wherein a first component of the system is disposed within the first and second branches bridging the main trunk and wherein the first and second elements have an opening aligned to face the main trunk, and implanting a second component in the main trunk such that at least a portion of the second component is located within the main trunk and at least a portion of the second component is located within the first component.

There is provided in accordance with an embodiment of the invention a multiple-component expandable endoluminal system for treating a lesion at a bifurcation including a self expandable tubular root member having a side-looking engagement aperture, a self expandable tubular trunk member including a substantially blood impervious polymeric liner secured therealong, both having a radially compressed state adapted for percutaneous intraluminal delivery and a radially expanded state adapted for endoluminal support, wherein root member and the trunk member are individually deployable, and wherein the trunk member is substantially non compressible along its longitudinal axis, and wherein the circumference of the side-looking engagement aperture is capable of having a substantially identical shape as the circumference of the body portion of the trunk member in its radially relaxed state, and wherein the trunk member is adapted to be inserted intraluminally through either ends of root member when in its deployable state and thereafter extraluminally substantially exiting through its side-looking engagement aperture and perpendicular thereto, and wherein the distal end of trunk member is adapted to be anchorably deployable through the side-looking engagement aperture.

BRIEF DESCRIPTION OF THE DRAWINGS

The present invention will be understood and appreciated more fully from the following detailed description, taken in conjunction with the drawings in which.

DESCRIPTION OF EMBODIMENTS

Figure 1:
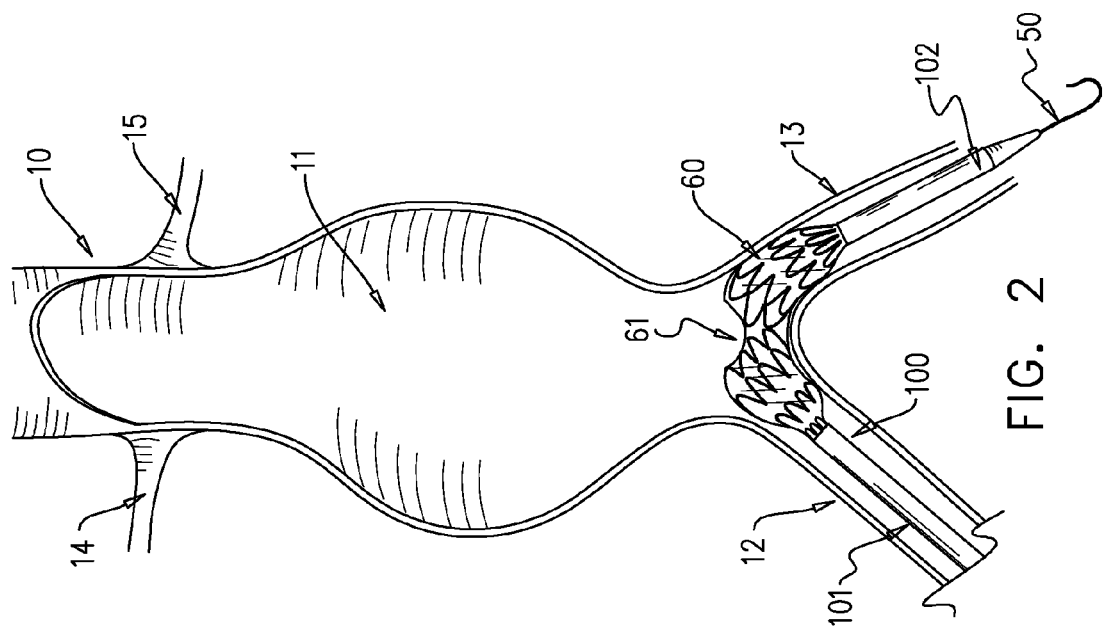
FIG. 1 is a simplified pictorial illustration of one possible insertion step in the deployment of an endoluminal graft in a non-limiting embodiment of the present invention.

Reference is now made to FIG. 1, which illustrates one possible insertion step in the deployment of a component of an endoluminal graft in a non-limiting embodiment of the present invention. A catheter 100 is percutaneously inserted into a bifurcation 12 (e.g., one iliac artery) extending from a main trunk 10, using conventional transluminal methods, such as with a guidewire 50. The catheter 100 is bent or deflected at an angle so that it passes the main lumen and is then introduced into a second bifurcation 13 (e.g., the second iliac artery) extending from the main trunk 10. FIG. 1 shows two branch arteries (arterial ostia) 14 and 15 branching from main trunk 10. There is an aneurysm 11 in the main trunk 10. Catheter 100 includes two catheter portions 101 and 102. Bifurcations 12 and 13 may also be referred to as arterial ostia 12 and 13.

Figure 2:
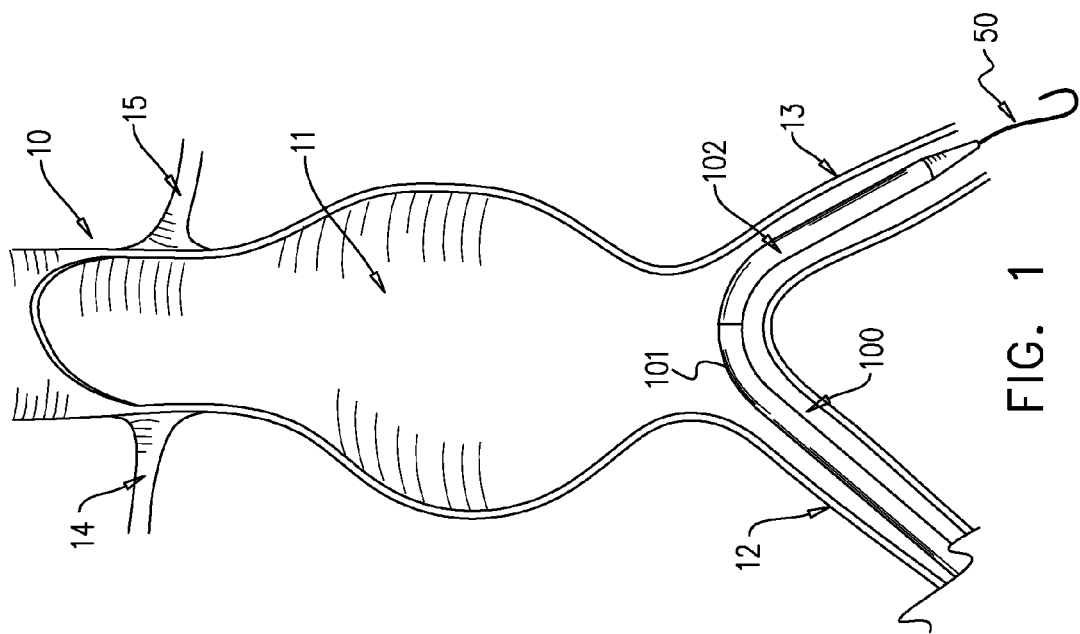
FIG. 2 is a simplified pictorial illustration of another deployment step of the endoluminal graft in a non-limiting embodiment of the present invention.
Figure 3:
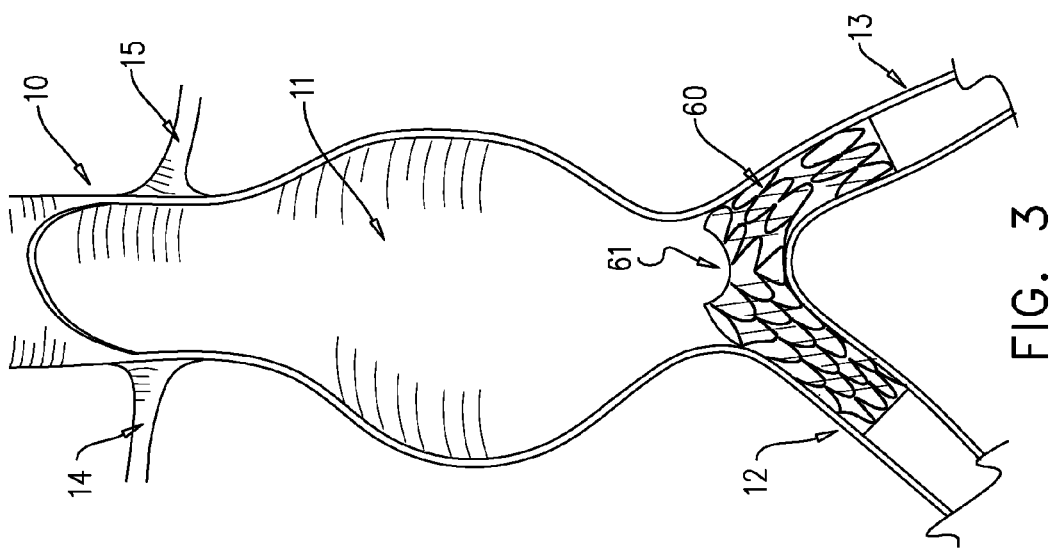
FIG. 3 is a simplified pictorial illustration of a stent graft component of the endoluminal graft free of its catheter and positioned such that it has an open end located within each bifurcation branch and an aperture is facing the main trunk.

Reference is now made to FIG. 2, which illustrates another deployment step of a component in a non-limiting embodiment of the present invention. Both the distal and proximal ends of the catheter portions 101 and 102, respectively, are moved in opposite directions (e.g., by suitable manipulation of guide wires attached thereto, not shown) so that a stent graft component 60 which is in a compressed state within the catheter is gradually freed. An aperture 61 in the stent graft component 60 is positioned by the operator (e.g., by suitable manipulation of a guide wire attached thereto, not shown, and assisted by imaging such as fluoroscopy) such that it faces the main trunk 10. FIG. 3 illustrates the stent graft component 60 free of its catheter and positioned such that it has an open end located within each bifurcation 12 and 13 respectively, while aperture 61 is facing the main trunk 10.

Figure 4:
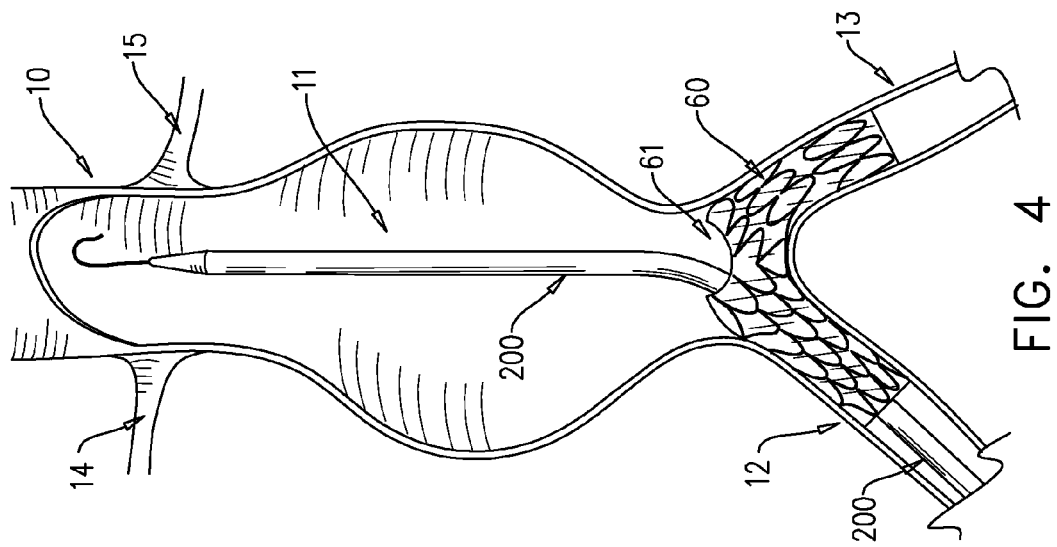
FIG. 4 is a simplified pictorial illustration of another deployment step of the endoluminal graft in a non-limiting embodiment of the present invention.

Reference is now made to FIG. 4, which illustrates another deployment step of a component in a non-limiting embodiment of the present invention. A second catheter 200 is inserted through one open end of the first stent graft component 60 so that its distal end extend through the aperture 61 in the first stent graft component and is located within the main trunk 10.

Figure 5:
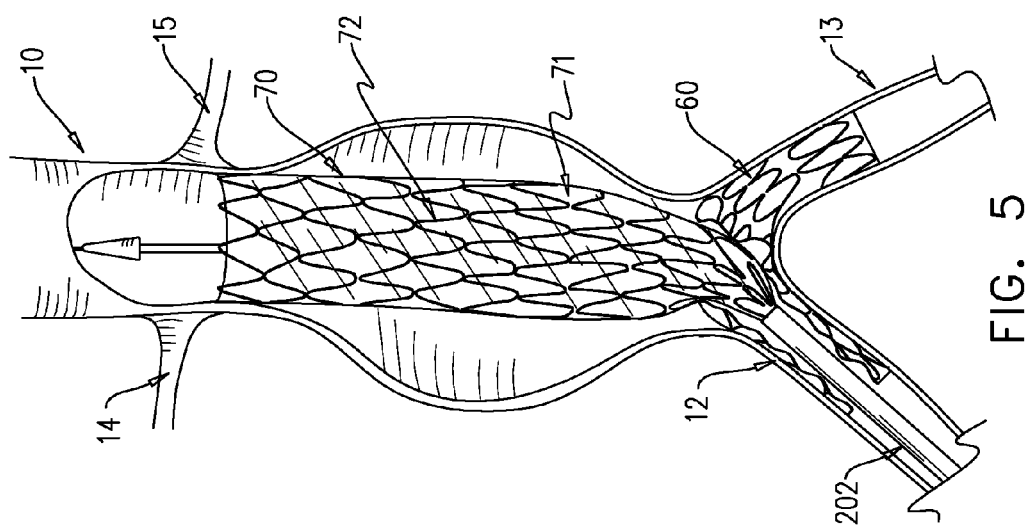
FIG. 5 is a simplified pictorial illustration of another deployment step of the endoluminal graft in a non-limiting embodiment of the present invention.
Figure 8:
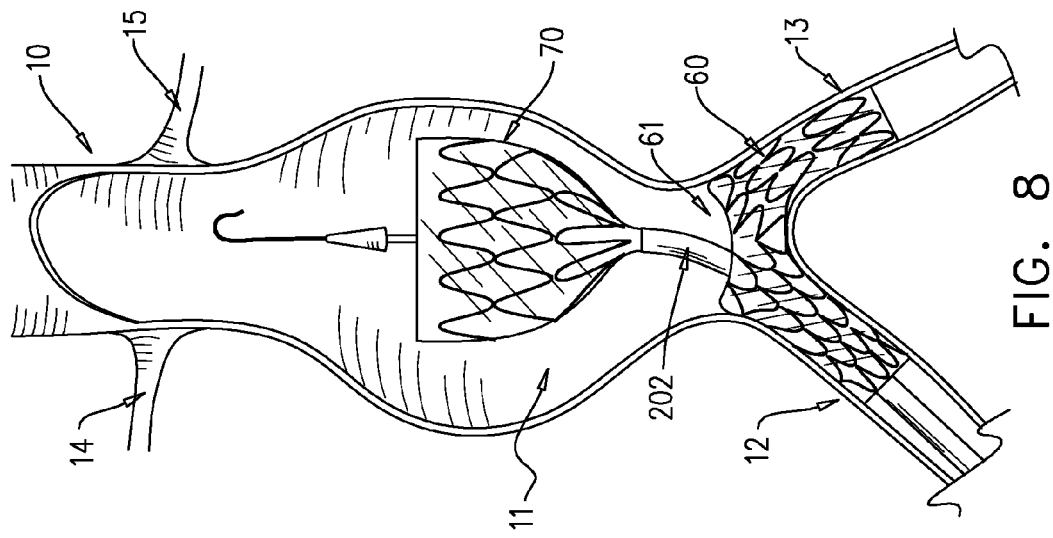
FIGS. 7-12 are simplified pictorial illustrations of another preferred embodiment of the present invention, wherein a catheter is inserted in a fashion similar to the embodiments of FIGS. 4-6.
Figure 7:
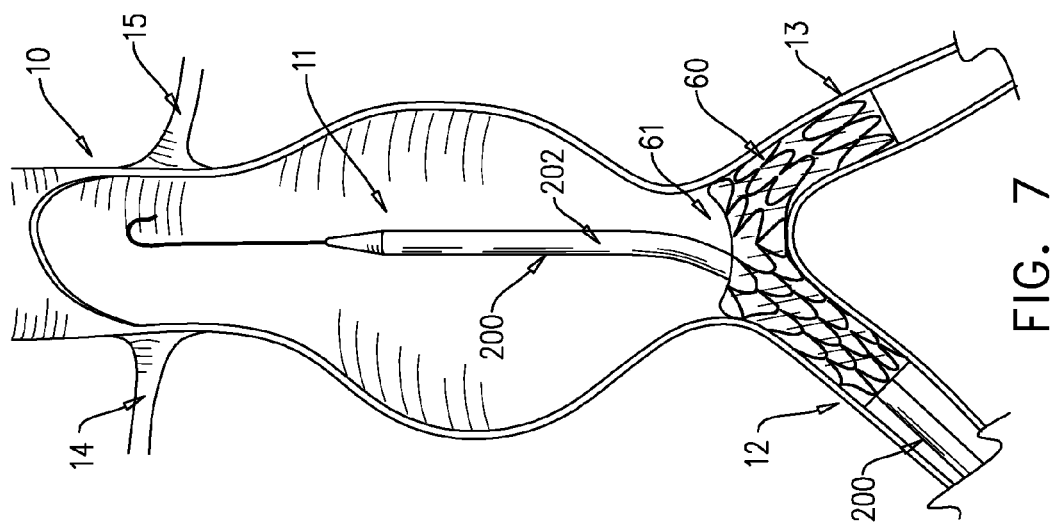
Figure 9:
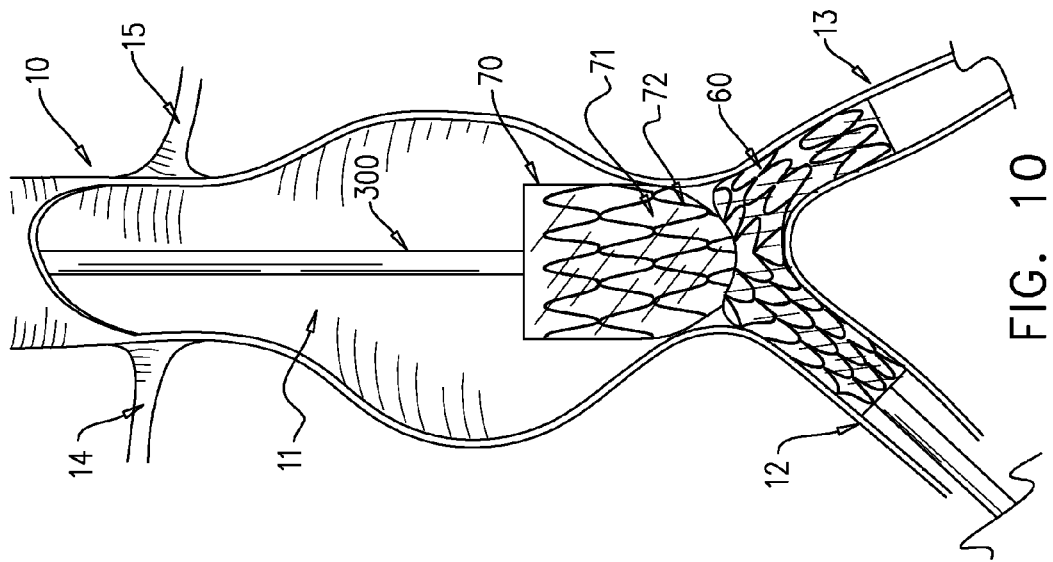
Figure 10:
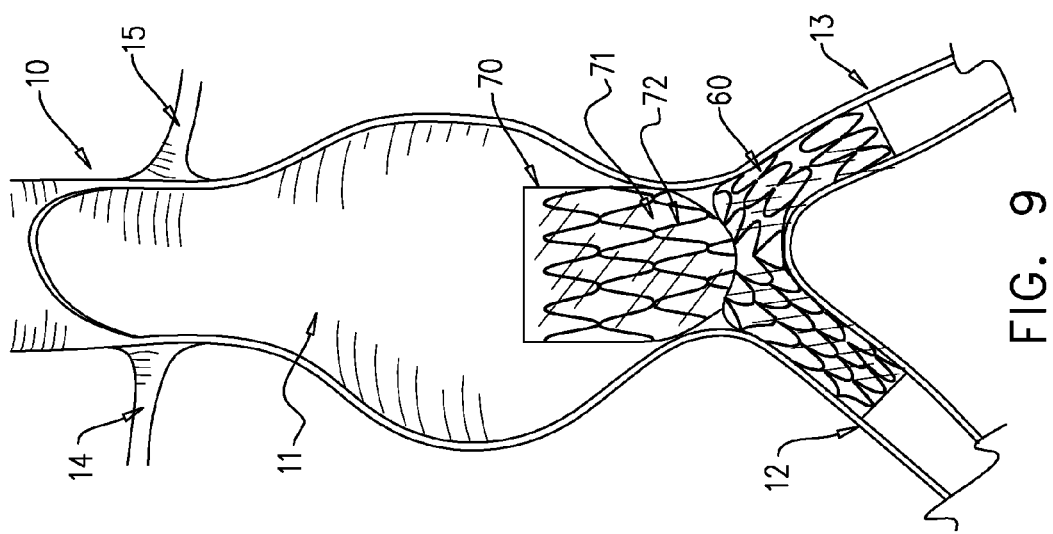

Reference is now made to FIG. 5, which illustrates another deployment step of a component in a non-limiting embodiment of the present invention. A second stent graft component 70 is gradually freed from its restraining catheter. Catheter outer tube 202 is withdrawn so that the stent graft component 70 is gradually free to expand in a radial direction, such that the graft component's distal end engages the walls of the main trunk 10 below arterial ostia 12 and 13, for example, the renal artery ostia. As the second stent graft component 70 is freed from the circumferential confines of the outer catheter tube 202, its proximal end engages the first stent graft component 60, thus anchoring the second stent graft component 70 to the first stent graft component 60.

Figure 6:
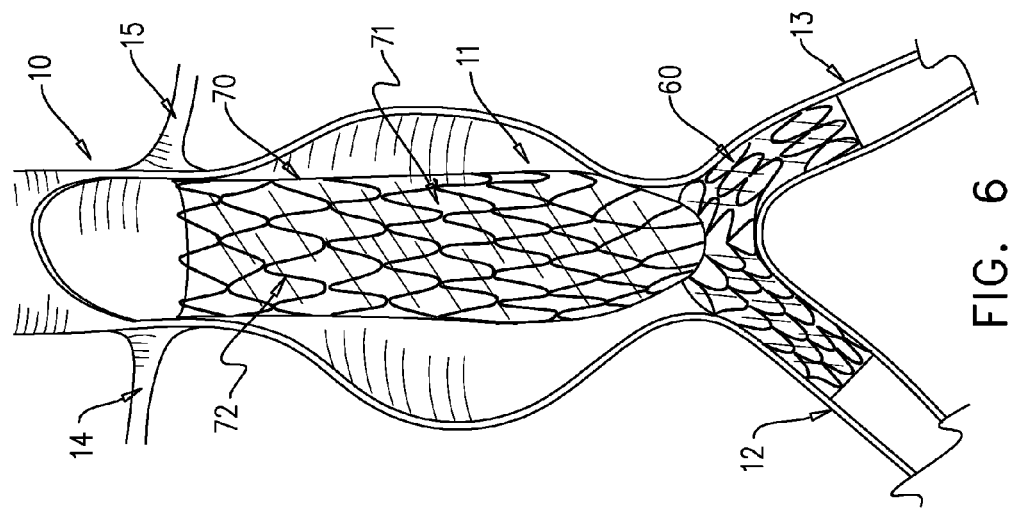
FIG. 6 is a simplified pictorial illustration of the stent graft system in place in accordance with an embodiment of the present invention.

FIG. 6 schematically illustrates the stent graft system in place, with the second stent graft component 70 having one end engaged radially against the wall of the main trunk 10 under arterial ostia 12 and 13, while its proximal end is concentrically located within one end of the first stent graft component 60.

FIGS. 7 through 12 illustrate another preferred embodiment of the present invention, wherein a catheter 70 is inserted in a fashion similar to the one described in FIGS. 4, 5 and 6. Stent graft component 70 is freed from its catheter 200 by retracting outer catheter tube 202 so that its distal end is free within the main trunk lumen. The distal end of said second stent graft component 70 may or may not touch the lumen walls of the main trunk. The proximal end of the second stent is located concentrically within one section of the first stent graft component 60 so that it is anchored by the first stent graft component. A catheter 300 is inserted in a similar fashion through an open end of the first stent graft component 60, and through the proximal end of the second stent graft component 70 located concentrically within the first stent graft component 60. Catheter 300 is inserted such that its proximal end extends beyond the open distal end of the second stent graft component 70. A third stent graft component 80 is released from the catheter so that its distal end radially engages the lumen walls of the main trunk 10. As the third stent graft component 80 is further released, its proximal end engages the second stent graft component 70 in a radial fashion, forming an anchoring point between the second stent graft component 70 and the third stent graft component 80.

Figure 12:
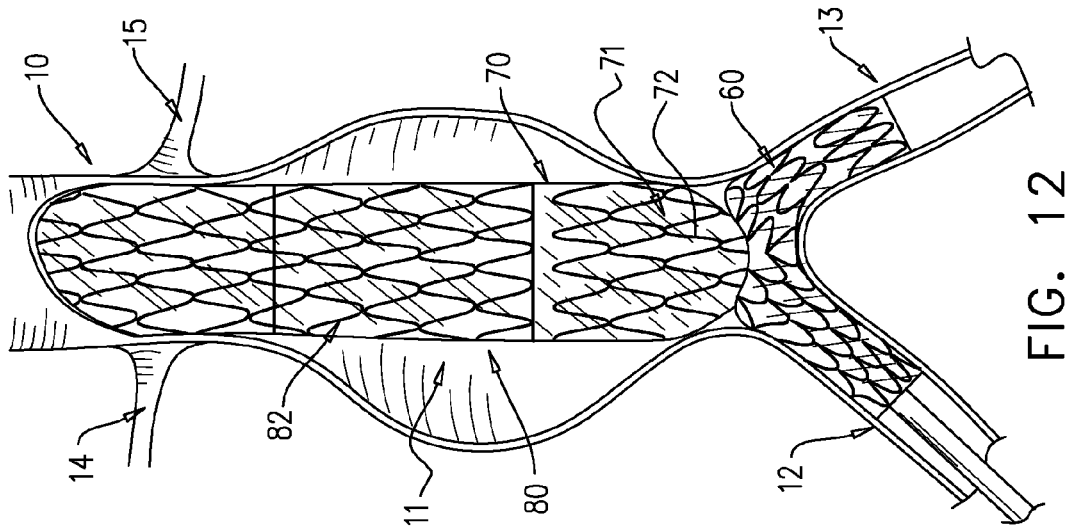
Figure 11:
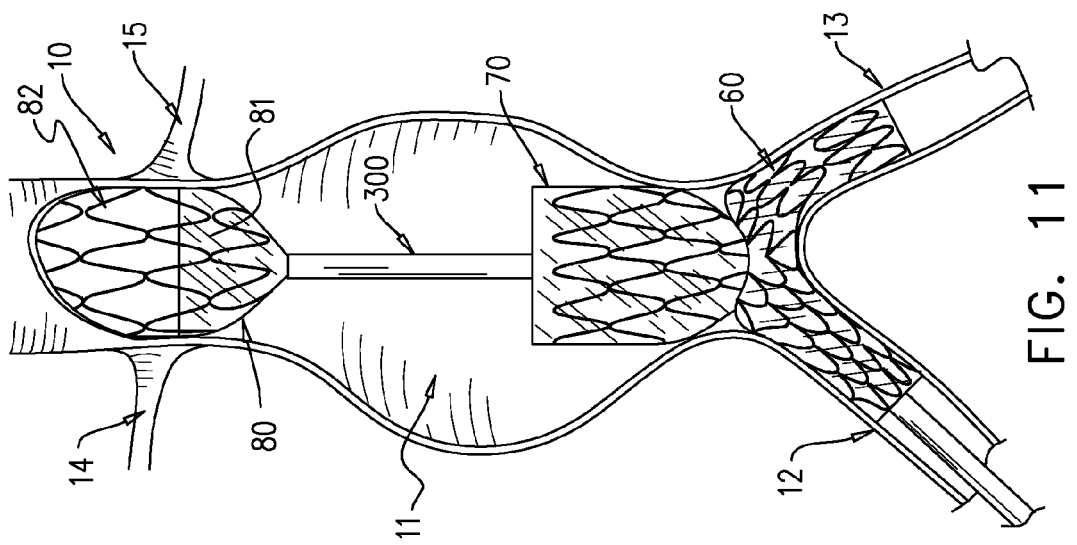

FIG. 12 shows elements of stent graft component 80 engaging the lumen walls of main trunk 10 such that support elements 82 engage the lumen wall above arterial ostia 12 and 13. Graft covering 81 does not extend above the arterial ostia so as not to block blood flow into the ostia 14 and 15.

Figure 13:
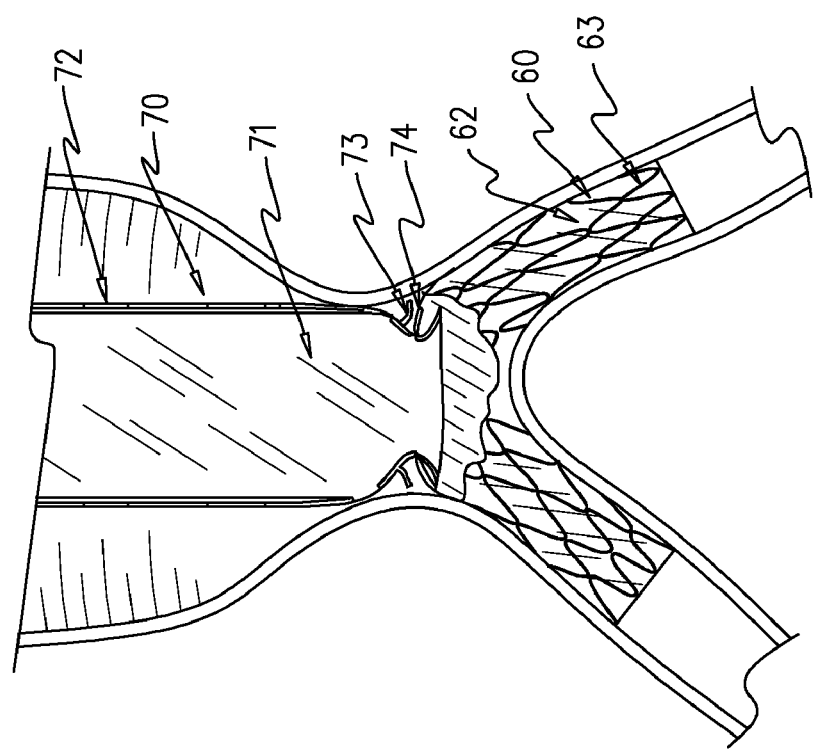
FIG. 13 is a simplified pictorial illustration of a non-limiting embodiment of an anchoring mechanism between first and second stent graft components.

FIG. 13 schematically illustrates a non-limiting embodiment of the anchoring mechanism between the first stent graft component 60 and the second stent graft component 70. In this embodiment, engagement arms 73 and 74 are located circumferentially on the second stent graft component 70 in at least two rows above and below aperture 61 in stent graft component 60. The rows of engagement arms 73 and 74 are formed so as to grasp both sides of aperture 61 in stent graft component 60. The two stent graft components are joined together as a result.

Figure 14:
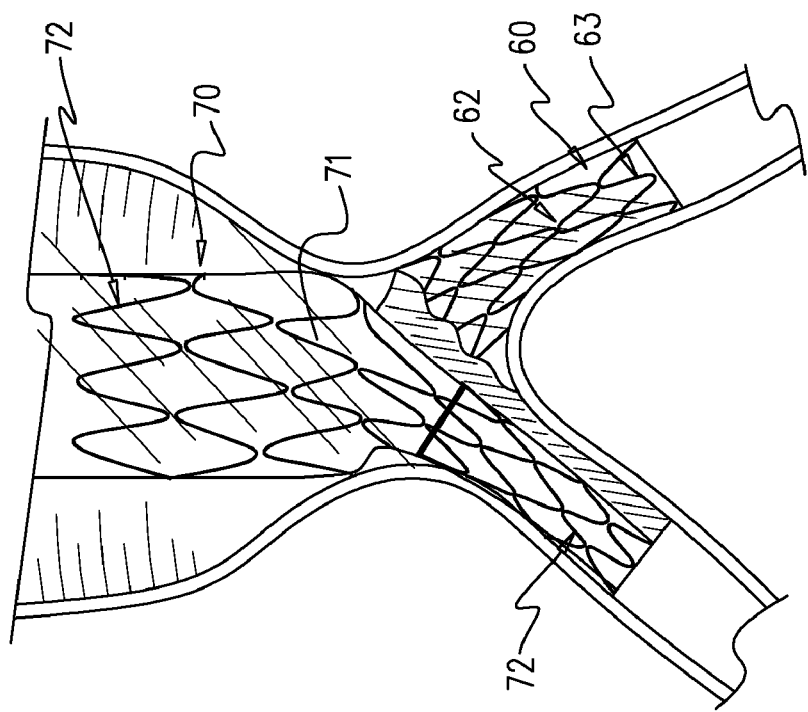
FIG. 14 is a simplified pictorial illustration of another non-limiting embodiment of an anchoring mechanism between stent graft components.

FIG. 14 schematically illustrates another non-limiting embodiment of the anchoring mechanism between stent graft component 60 and stent graft component 70 whereby the proximal end of stent graft component 70 is concentrically located within at least a portion of stent graft component 60 with a section of the second stent graft component 70 extending through the aperture 61 and within a portion of stent graft component 60. The graft covering 71 does not necessarily extend throughout the length of stent graft component 70.

Figure 15A:
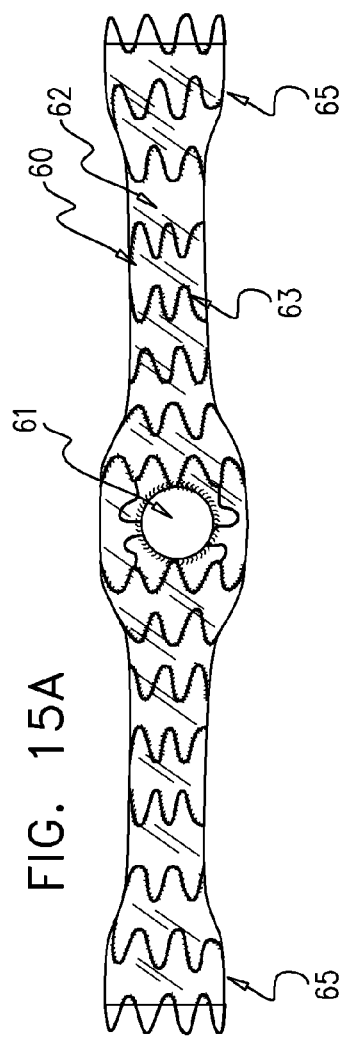
FIG. 15A is a simplified pictorial illustration of a non-limiting embodiment of a stent graft component with an aperture evident in the graft material.

FIG. 15A schematically illustrates a non-limiting embodiment of stent graft component 60 wherein aperture 61 is evident in the graft material covering component 61. The graft covering 62 may be connected to support section 63 by means of sutures, adhesives or any suitable means. Aperture 61 in the graft covering 62 may be equal in size to the aperture affected in support structure 63. Flaring may be introduced to component ends 65 in order to better engage a body lumen (not shown) when implanted.

Figure 15B:
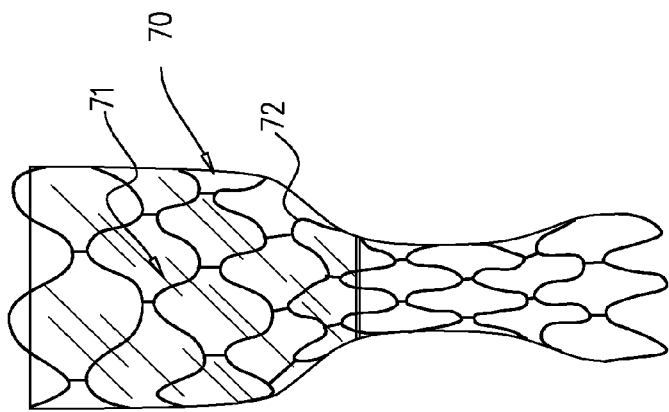
FIGS. 15B and 15C are simplified pictorial illustrations of a non-limiting embodiment of stent graft component wherein the component includes sections with varying diameters.
Figure 15C:
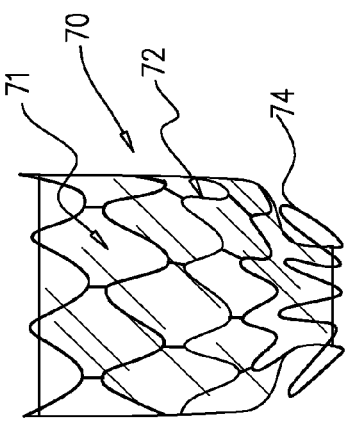

FIGS. 15B and 15C schematically illustrates a non-limiting embodiment of stent graft component 70 wherein component 70 may have include sections with varying diameters, so that a portion of component 70 may be deposited within a section of component 60 (not shown). FIG. 15C shows another embodiment wherein circumferential engagement arms 74 may be formed so as to engage portions of component 60 (not shown) so as to anchor both components together.

Figure 16A:
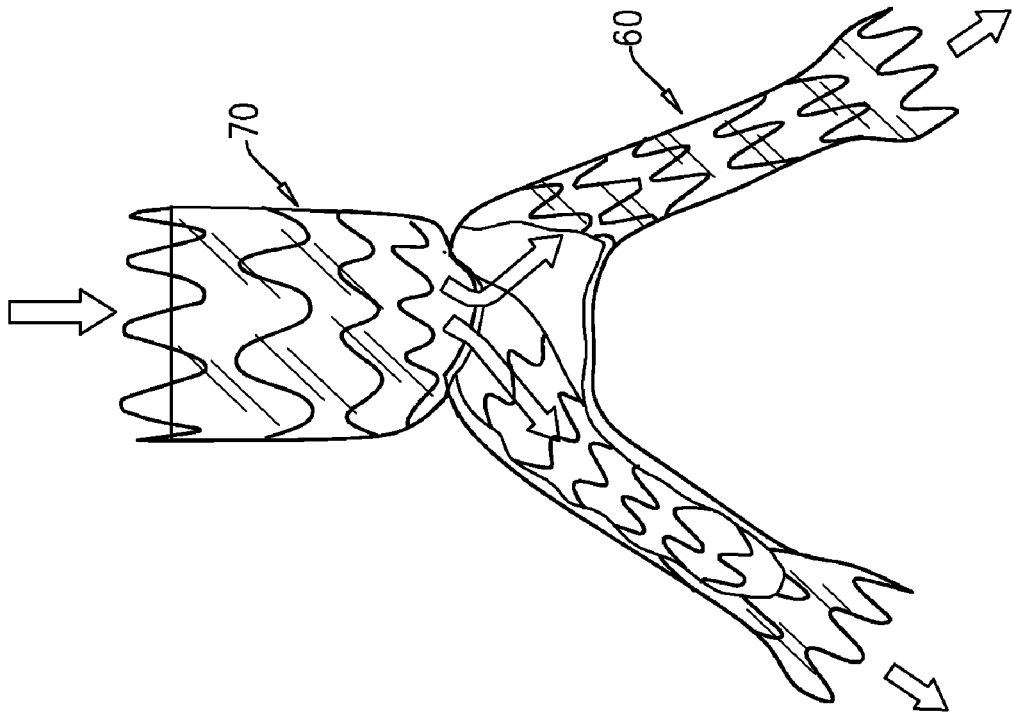
FIGS. 16A and 16B are simplified pictorial illustrations of the flow of blood through the joined stent graft components.
Figure 16B:
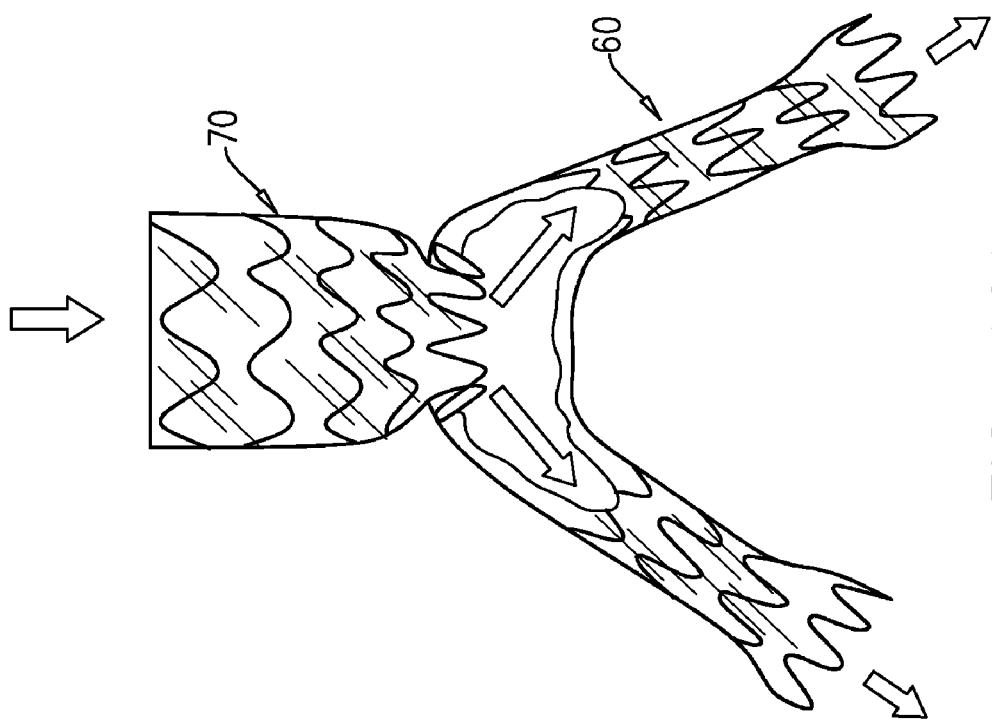

FIGS. 16A and 16B show the flow of blood through the joined stent graft components 60 and 70. It is important to allow blood flow to both sides of component 60 so as not to cause ischemia. FIG. 16B illustrates that component 70 is not covered throughout by a graft covering so as to allow blood flow to both sides.

The scope of the present invention includes both combinations and subcombinations of the features described hereinabove as well as modifications and variations thereof which would occur to a person of skill in the art upon reading the foregoing description and which are not in the prior art.

What is claimed is:

1. A stent graft system comprising:
    a first component, which comprises a tubular structure, which comprises a first support element and a first covering element attached to said first support element, two sides of said first component being positionable, respectively, in first and second branches that branch from a main trunk of a subject, wherein said first covering element is shaped so as to define an opening arranged to face said main trunk; and
    a second component, which comprises a second support element and a second covering element attached to said second support element, said second component partially disposed within said first component, extending out of said first component through said opening,
    wherein said second component comprises a proximal segment and a distal segment, said proximal segment being anchorably disposed within exactly one of said two sides of said first component, such that said proximal segment engages said exactly one side, and wherein said distal segment of said second component extends out of said first component through said opening, and
    wherein said second covering element only partially covers said second support element so as to allow blood flow to both of said two sides of said first component.

2. The stent graft system according to claim 1, wherein said first component is adapted for transluminal delivery for transport to a site within a body lumen by being radially compressed from a larger cross-section to a smaller cross-section.

3. The stent graft system according to claim 1, wherein said second component is adapted for transluminal delivery for transport to a site within a body lumen by being radially compressed from a larger cross-section to a smaller cross-section.

4. The stent graft system according to claim 1, wherein said first covering element only partially covers said first support element.

5. The stent graft system according to claim 1, wherein said first and second components are radially compressible from respective larger cross-sections to respective smaller cross-sections, wherein said first and second components are adapted for transluminal delivery for transport to a site within a body lumen, and wherein said second component is adapted for transluminal delivery through said first component when said first component assumes its larger cross-section.

6. The stent graft system according to claim 5, wherein said first component, when it assumes its larger cross-section, is dimensioned to intraluminally fit iliac arteries of said subject, and wherein said second component, when it assumes its larger cross-section, is dimensioned to intraluminally fit an abdominal aorta of said subject.

7. The stent graft system according to claim 1, wherein said second covering element substantially covers said distal segment but does not generally cover said proximal segment.

8. The stent graft system according to claim 1, wherein said second covering element substantially covers said distal segment, covers a proximal portion of said proximal segment, and does not cover a distal portion of said proximal segment.

9. The stent graft system according to claim 1, wherein said second component includes sections having varying diameters, such that a portion of said second component is disposable within a section of said first component.

10. The stent graft system according to claim 1, wherein a diameter of a distal section of said distal segment not disposed within said first component is greater than a diameter of said opening, and wherein said diameter of said distal section increases as said distal section exits from said opening.

11. The stent graft system according to claim 1, wherein a section of said second covering element extends through said opening and within a portion of said first component when said proximal segment is anchorably disposed within said exactly one of said two sides of said first component.

12. The stent graft system according to claim 1, wherein said proximal segment of said second component is concentrically located within at least a portion of said first component when said proximal segment is anchorably disposed within said exactly one of said two sides of said first component.

13. The stent graft system according to claim 1, wherein said first component widens in a vicinity of said opening.

14. The stent graft system according to claim 1, wherein said first component is configured such that a perimeter of said opening is less than a perimeter of supports of said first component surrounding said opening, such that a portion of said first covering element surrounding said opening extends from said supports towards said opening.

15. The stent graft system according to claim 1, wherein said second component has a generally cylindrical form.

16. A method comprising:
implanting, respectively in first and second iliac arteries that branch from an abdominal aorta of a subject, two sides of a first component of a stent graft system, which first component includes a first support element and a first covering element attached to said first support element, such that an opening defined by said first covering is aligned to face said abdominal aorta; and
thereafter, implanting a second component of said system, which second component includes a second support element and a second covering attached to said second support element, by:
transluminally advancing a catheter tube through one open end of exactly one of said two sides of said first component and out through the opening into the abdominal aorta, while said second component is radially compressed within said catheter tube, and
withdrawing said catheter tube so that (a) at least a distal segment of said second component is freed from said catheter tube and radially expands within said abdominal aorta, and (b) thereafter, at least a proximal segment of said second component is freed from said catheter tube and radially expands within said exactly one of said two sides of said first component, thereby anchoring said at least a proximal segment of said second component to said first component,
wherein said second covering element only partially covers said second support element so as to allow blood flow to both of said two sides of said first component.

17. The method according to claim 16, wherein said second covering element substantially covers said distal segment but does not generally cover said proximal segment.

18. The method according to claim 16, wherein said second covering element substantially covers said distal segment, covers a proximal portion of said proximal segment, and does not cover a distal portion of said proximal segment.

19. The method according to claim 16, wherein said second component includes sections having varying diameters, such that a portion of said second component is disposable within a section of said first component.

20. The method according to claim 16, wherein anchoring said at least a proximal portion of said second component comprises disposing said second component such that a section of said second covering element extends through said opening and within a portion of said first component.

21. The method according to claim 16, wherein anchoring said at least a proximal segment of said second component comprises concentrically locating said at least a proximal segment of said second component within at least a portion of said exactly one of said two sides of said first component.

22. The method according to claim 16,
wherein said catheter tube is a second catheter tube, and
wherein implanting said first component comprises transluminally delivering said first component by:
advancing a first catheter tube into said first and second iliac arteries, while said first component is radially compressed within said first catheter tube, and
thereafter freeing said first component from said first catheter tube such that said first component radially expands in said first and second iliac arteries.

23. The method according to claim 16, wherein said second component is generally cylindrical.

24. The method according to claim 16, wherein withdrawing said catheter tube comprises withdrawing said catheter tube such that said distal segment that radially expands within said abdominal aorta has a diameter that (a) is greater than a diameter of said opening, and (b) increases as said distal segment exits from said opening.

* * * * *